(12) United States Patent
Littich et al.

(10) Patent No.: US 9,266,918 B2
(45) Date of Patent: Feb. 23, 2016

(54) ALKENYL GLYCOSIDES AND THEIR PREPARATION

(71) Applicant: Elevance Renewable Sciences, Inc., Woodridge, IL (US)

(72) Inventors: Ryan A. Littich, Shorewood, IL (US); Jonathan Brekan, Chicago, IL (US); Timothy Montavon, Palatine, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 14/202,863

(22) Filed: Mar. 10, 2014

(65) Prior Publication Data

US 2014/0275506 A1 Sep. 18, 2014

Related U.S. Application Data

(60) Provisional application No. 61/782,459, filed on Mar. 14, 2013.

(51) Int. Cl.
*C07H 15/10* (2006.01)
*C07H 1/00* (2006.01)

(52) U.S. Cl.
CPC . *C07H 15/10* (2013.01); *C07H 1/00* (2013.01)

(58) Field of Classification Search
None
See application file for complete search history.

(56) References Cited

U.S. PATENT DOCUMENTS

| 5,374,716 A | * | 12/1994 | Biermann et al. | 536/18.6 |
| 5,480,979 A | * | 1/1996 | Weuthen et al. | 536/18.6 |
| 2002/0007050 A1 | * | 1/2002 | Eskuchen et al. | 536/18.5 |

* cited by examiner

*Primary Examiner* — Layla Berry
(74) *Attorney, Agent, or Firm* — Robert S. Dailey

(57) ABSTRACT

An alkenyl glycoside is prepared by reacting a metathesis-derived unsaturated fatty alcohol containing 10 to 30 carbon atoms with either (1) a reducible monosaccharide or composition hydrolyzable to a reducible monosaccharide, or (2) a hydrocarbyl glycoside produced by reacting an alcohol containing up to 6 carbon atoms with a reducible monosaccharide or composition hydrolyzable to a reducible monosaccharide. Each of these reactions is performed in the presence of an acid catalyst and under conditions sufficient to form the alkenyl glycoside or hydrocarbyl glycoside. The preferred alkenyl glycosides are 9-decen-1-yl glycoside; 9-dodecen-1-yl glycoside; 9-tridecen-1-yl glycoside; 9-pentadecen-1-yl glycoside; 9-octadecen-yl glycoside; or 9-octadecen-1,18-diyl glycoside.

11 Claims, No Drawings

ALKENYL GLYCOSIDES AND THEIR PREPARATION

CROSS-REFERENCE TO RELATED APPLICATIONS

This application claims the benefit of U.S. Provisional Application No. 61/782,459 filed Mar. 14, 2013, the entire contents of which are hereby incorporated by reference.

BACKGROUND

Surfactants based on hydrocarbyl glycosides are gaining increasing attention due to their advantages over other surfactants with regard to notable dermatological properties and good compatibility with standard products, as well as their favorable environmental profile. In addition, their low toxicity, good biocompatibility and fast biodegradation make this class of molecules very attractive, not only for personal care products but also for a large range of technical applications.

Compositionally, hydrocarbyl glycosides are fatty alcohol-glycose adducts which are covalently bound by an acetal linkage at the anomeric carbon of the glycose moiety. These can be used as nonionic surfactants that provide detergency, foaming, emulsifying, and wetting properties that are comparable to those of other nonionic surfactants.

In general, two different processes are practiced in the commercial production of alkyl polyglucosides, direct glycosidation and transglycosidation. Both manufacturing processes operate via Brönsted acid-catalyzed condensation at the anomeric (aldehydic) carbon of a monosaccharide, commonly referred to as Fischer glycosidation.

Direct glycosidation can be characterized by the coupling of a high molecular weight alcohol with glycose, without the formation of an intermediate low molecular weight alcohol-glycose adduct.

Transglycosidation, conversely, proceeds through a comparatively lower molecular weight, transient alkyl glycoside en route to the desired alkyl glycoside product.

Improvements in metathesis catalysts (see J. C. Mol, *Green Chem.* 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As this article explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates olefins and unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets. Elevance Renewable Sciences, Inc. has described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecene, 9-decenoic acid, and 9-undecenoic acid.

SUMMARY

In one aspect, an alkenyl glycoside is prepared by reacting a metathesis-derived unsaturated fatty alcohol containing 10 to 30 carbon atoms with either (1) a reducible monosaccharide or composition hydrolyzable to a reducible monosaccharide, or (2) a hydrocarbyl glycoside produced by reacting an alcohol containing up to 6 carbon atoms with a reducible monosaccharide or composition hydrolyzable to a reducible monosaccharide. Each of these reactions is performed in the presence of an acid catalyst and under conditions sufficient to form the alkenyl glycoside or hydrocarbyl glycoside.

In accordance with another aspect of the invention, a composition is provided comprising 9-decen-1-yl glycoside; 9-dodecen-1-yl glycoside; 9-tridecen-1-yl glycoside; 9-pentadecen-1-yl glycoside; 9-octadecen-1-yl glycoside; or 9-octadecen-1,18-diyl glycoside.

DETAILED DESCRIPTION

As used herein, the term "hydrocarbyl" or "hydrocarbyl group," when referring to groups attached to the remainder of a molecule of a metathesis-derived hydrocarbyl unsaturated ester or metathesis-derived alcohol refers to one or more groups having a purely hydrocarbon or predominantly hydrocarbon character. These groups may include: (1) purely hydrocarbon groups (i.e., aliphatic (alkyl), alicyclic, aromatic, branched, aliphatic- and alicyclic-substituted aromatic, aromatic-substituted aliphatic and alicyclic groups, as well as cyclic groups wherein the ring is completed through another portion of the molecule (that is, any two indicated substituents may together form an alicyclic group)); (2) substituted hydrocarbon groups (i.e., groups containing non-hydrocarbon substituent such as hydroxy, amino, nitro, cyano, alkoxy, acyl, halo, etc.); and (3) hetero groups (i.e., groups which contain atoms, such as N, O or S, in a chain or ring otherwise composed of carbon atoms). In general, no more than about three substituents or hetero atoms, or no more than one, may be present for each 10 carbon atoms in the hydrocarbyl group. The hydrocarbyl group may contain one, two, three or four carbon-carbon double bonds.

As used herein, the terms "natural oils," "natural feedstocks," or "natural oil feedstocks" may refer to oils derived from plants or animal sources. The term "natural oil" includes natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

As used herein, the term "natural oil derivatives" may refer to the compounds or mixture of compounds derived from the natural oil using any one or combination of methods known in the art. Such methods include but are not limited to saponification, fat splitting, transesterification, esterification, hydrogenation (partial or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, the terms "metathesize" and "metathesizing" may refer to the reacting of a feedstock in the presence of a metathesis catalyst to form a "metathesized product" comprising a new olefinic compound. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, the terms "ester" and "esters" may refer to compounds having the general formula: R—COO—R', wherein R and R' denote any organic compound (such as alkyl, aryl, or silyl groups), including those bearing heteroatom containing substituent groups. In certain embodiments, R and R' denote alkyl or aryl groups. In certain embodiments, the term "ester" or "esters" may refer to a group of compounds with the general formula described above, wherein the compounds have different carbon lengths.

A starting composition in the method described herein comprises a reducible monosaccharide. Such reducible monosaccharides are the hexoses and pentoses. Typical examples include glucose, mannose, galoctose, talose, allose, altrose, idose, arabinose, xylose, lyxose, ribose, and their monohydrate forms. The preferred reducible monosaccharide is glucose monohydrate. Compounds that are hydrolyzable to reducible monosaccharides include starch, maltose sucrose, lactose, melibiose, raffinose, methyl glucosides, butyl glucosides and anhydro sugars such as laevoglucose, and 1,6-anhydroglucofuranose.

While all of the reducible monosaccharides and compositions hydrolyzable to reducible monosaccharides can be employed in the method described herein, solely for the sake of convenience, embodiments will be illustrated and described in terms of the use in it of glucose as the representative reducible monosaccharide.

The glycose that is employed in the method described herein can be employed in any of the compositions in which it is conventionally available. Thus, glycose-containing compositions such as anhydrous glucose, glucose monohydrate, and concentrated syrupy aqueous solutions of glucose, can be employed. In addition, glucose-forming compositions such as starch, which upon hydrolysis form glucose, can also be employed in the method described herein.

When using the transglycosidation method, the lower weight alcohol that is reacted with the reducible monosaccharide or composition hydrolyzable to a reducible monosaccharide contains up to 6 carbon atoms, preferably from 1 to 5 carbon atoms, and more preferably 4 carbon atoms. This lower weight alcohol may be saturated or unsaturated, but preferably is saturated. Preferably, the lower weight alcohol is a straight-chain alcohol. Most preferably, the lower weight alcohol is n-butanol.

If direct glycosidation is used, the reducible monosaccharides and compositions hydrolyzable to reducible monosaccharides are reacted directly with the unsaturated fatty alcohol.

Typically, the fatty alcohols employed in commercial reactions are made by reducing the corresponding fatty acids or esters, often by catalytic hydrogenation. The fatty acids or esters used to make fatty alcohols are usually made by hydrolysis of triglycerides, which typically are from animal or vegetable fats. Consequently, the fatty portion of the acid or ester will typically have 6-22 carbons with a mixture of saturated and internally unsaturated chains. Depending on the source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic, linoleic, and α-linolenic acids. The unsaturation in these acids typically has either exclusively or predominantly cis-configuration. Thus, traditional sources of fatty acids and esters that are used to produce unsaturated fatty alcohols, and the glycosides produced from them, often have predominantly or exclusively cis-isomers and lack relatively short-chain (for example, $C_{10}$ or $C_{12}$) unsaturated fatty portions.

It would be desirable to generate fatty acids and esters having shorter chains and substantially more trans-isomers which could be used to produce unsaturated fatty alcohols, and the alkenyl glycosides produced from them, also having shorter chains and substantially more trans-isomers. The resulting alkenyl glycosides should have substantially improved performance characteristics.

An elevated proportion of trans-isomer content, relative to the usual predominantly or all-cis configuration of the conventionally derived hydrocarbyl unsaturated fatty alcohol, imparts different physical properties to the metathesis-derived unsaturated alcohols produced and to the alkenyl glycosides produced from them. These physical property differences include, for example, modified physical form, melting range, compactability, and other important properties. These differences allow formulators that use the alkenyl glycosides produced by the method described herein greater latitude or expanded choice as they use them in cleaners, detergents, personal care, agricultural uses, specialty foams, and other end uses.

Unsaturation in the hydrocarbyl or fatty moiety of the alkenyl glycosides produced by the method described herein can also impart advantages not seen in their saturated counterparts. For example alkenyl glycosides produced by the method described herein have lower melting points than do their saturated counterparts, which therefore reduce liquid crystal formation in their aqueous solutions. Alkenyl glucoside produced by the methods described herein are also more soluble in organic solvents and in their aqueous solutions, and therefore afford higher critical micelle concentration values, relative to their analogous saturated counterparts. Moreover, alkenyl glycosides produced by the method described herein display relatively lower inherent viscosities in their aqueous solutions than do their analogous saturated counterparts. By contrast to aqueous solutions of saturated alkyl glycosides prepared from conventionally sourced fatty alcohols, aqueous solutions of alkenyl glycosides prepared from metathesis-derived fatty alcohols display distinct lipid polymorphism behavior over the broad range of surfactant concentrations employed. This distinctive performance can be rationalized on the basis of differences between the micelle structures of alkenyl glycosides prepared from metathesis-derived unsaturated fatty alcohols and alkyl glycosides prepared from conventionally sourced fatty alcohols. Also, unsaturation in the fatty alkyl moiety of the alkenyl glycosides prepared from metathesis-derived fatty acids affects the hydrophilic/lipophilic balance value which can have a positive impact on its cleaning, emulsification, and dispersancy properties. Because crystallinity is disrupted by the presence of a carbon-carbon double bonds, alkenyl glycosides prepared from metathesis-derived alcohols can be concentrated and formulated at higher active levels—sometimes much higher—than their saturated counterparts. Thus, the seemingly minor structural change to an unsaturated product can enable shipment of more concentrated products, reduce or eliminate the need for special handling equipment, and/or ultimately provide substantial cost savings.

The unsaturated fatty alcohol employed in the method described herein is metathesis-derived and contains from 10 to 30 carbon atoms, preferably from 10 to 20 carbon atoms, more preferably 10, 12, 13, 15, or 18 carbon atoms, and most preferably 10, 12, or 18 carbon atoms. Preferably the unsaturated metathesis-derived alcohol is a straight chain alcohol. The metathesis-derived unsaturated fatty alcohol preferably is 9-decen-1-ol, 9-dodecen-1-ol, 9-tridecen-1-ol, 9-pentadecen-1-ol, 9-octadecen-1-ol or 9-octadecen-1,18-diol, and more preferably is 9-decen-1-ol, 9-dodecen-1-ol or 9-octadec-9-en-1-ol or 9-octadecen-1,18-diol. Ideally the unsaturated alcohol has the general structure:

R—CH=CH—(CH$_2$)$_7$—CH$_2$OH wherein R is H, (CH$_2$)$_{1-9}$CH$_3$, or (CH$_2$)$_{1-9}$CH$_2$OH.

In addition to alkyl monoglycoside, the Fischer glycosidation process, by which alkyl glycosides are typically manufactured commercially, often generates alkyl diglycosides, alkyl triglycosides and higher oligomeric alkyl glycosides. Such oligomeric alkyl glucosides are the result of a competitive glycosidation reaction between hydroxyl groups in the initially-formed alkyl monoglycoside and the reducible saccharide, generally shown below:

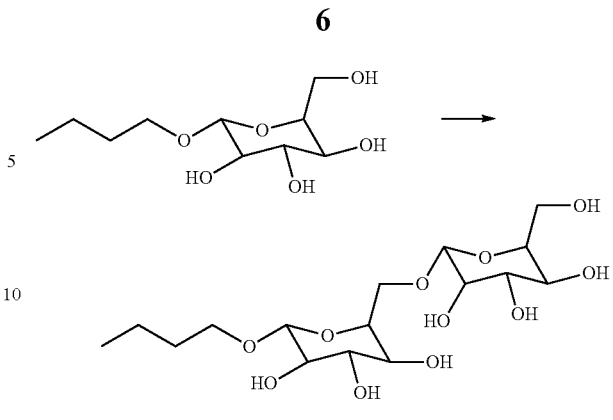

For some commercial applications, these oligomeric alkyl glycosides are acceptable. For this reason, some commercial surfactants prepared by this method are called alkyl polyglycosides. As used herein, the term alkenyl glycoside is intended to cover both monoglycosides and polyglycosides.

Alternatively, it may be desirable to minimize the formation of alkyl polyglycosides. To do this, a large excess of fatty alcohol relative to the amount of reducible saccharide present is employed, during the glycosidation process. Drastically increasing the concentration of fatty alcohol in the reaction promotes the desired glycosidation pathway and impedes the competitive glycosidation of the alkyl monoglucoside, as it is formed.

The molar ratio of alcohol-to-the reducible monosaccharide or composition hydrolyzable to reducible monosaccharide is preferably from about 3:1 to about 10:1 and more preferably from about 5:1 to about 6:1.

The particular molar ratio chosen depends upon the desired average degree of polymerization of the reducible monosaccharide or composition hydrolyzable to a reducible monosaccharide onto the particular alcohol. The degree of polymerization (DP) represents the average number of moieties derived from the reducible monosaccharide or composition hydrolyzable to a reducible monosaccharide that are attached to each hydrocarbyl chain of the hydrocarbyl glycoside produced. Generally, as the alcohol-to-glycoside ratio is increased, the degree of polymerization decreases. Likewise, as this ratio is decreased, the degree of polymerization increases. Mathematically, DP=1+(f−1)/RE where f equals 5 and is the number of hydroxyls on the ring of the reducible monosaccharide or composition hydrolyzable to a reducible monosaccharide in the cyclic acetal form, empirically R varies between about 1.5-2.5 and is the binding reactivity of the fatty alcohol for the reducible monosaccharide or composition hydrolyzable to a reducible monosaccharide relative to the average reactivity of available non-anomeric hydroxyl groups of the reducible monosaccharide or composition hydrolyzable to a reducible monosaccharide and $F_T$ is the mole ratio of alcohol to available the reducible monosaccharide or composition hydrolyzable to a reducible monosaccharide.

Preferably, the mole ratio is chosen to allow the production of an alkenyl glycoside product having a degree of polymerization between about 1.2 and 2.2. Low mole ratios should be avoided for optimized reaction control. This is because under these conditions two irreversible and undesirable side reactions may take place. For example, elevated levels of polymers may form, especially during the latter stages of the reaction. This results in excessive foaming and in the loss of the reducible monosaccharide and of compositions hydrolyzable to reducible monosaccharide in the reaction material, actually causing an increase in $F_T$ and hence a decrease in degree of polymerization. The second reaction involves the dehydration of the reducible monosaccharide and of compositions hydrolyzable to reducible monosaccharide into condensation products, which are, or later yield, color bodies which would contaminate the product.

The temperature for carrying out the reaction may vary between about 85° C. and about 120° C., preferably between about 95° C. and about 115° C. If a temperature significantly greater than 120° C. is used, the side reactions increase faster than the primary reaction. This causes an increase in the formation of unwanted color bodies. The temperature also should not be significantly below 85° C. This is because such a reduced temperature would cause an unacceptable reduction in reaction rate.

The reaction should take place in an environment which facilitates the removal of the more volatile reaction byproducts. This environment may be conveniently maintained by reducing the pressure under which the reaction occurs. This reduction of pressure enables more volatile reaction by-products to be evaporated from the reaction mixture. Preferably, such a reduction in pressure is achieved by applying a vacuum to the reaction system. Preferred apparatus for applying vacuum to the reaction system includes steam jets or mechanical vacuum pumps. The final vacuum preferably should be applied at a pressure between about 20 mm Hg and about 100 mm Hg. This is especially desirable when water is a reaction by-product. If the absolute pressure is allowed to exceed 100 mm Hg to a significant extent, the water produced in the reactions may not be removed to the extent required to prevent the buildup of a separate water phase in the reaction system. If this occurred, the production of unacceptable amounts of polydextrose could ensue and the forward glycosidation reaction could be retarded due to its reversible nature. If the pressure is kept significantly below 20 mm Hg, co-distillation of lower alcohols may result. In addition, almost all of the water remaining in the reaction system could be evaporated. Under these circumstances, reducible monosaccharides and compositions hydrolyzable to reducible monosaccharides degrade faster, and the degradation products more rapidly form unacceptable levels of color bodies. An additional problem with pressures below 20 mm Hg is the inability to economically condense water vapor and the associated problems of high volumes of non-condensed vapors or contamination of vacuum pump fluids.

An acid catalyst is employed in the method described herein. The catalyst is used in an amount between about 0.05% and about 5%, preferably between about 0.5% and about 2.0%, based upon the amount of glucose or glucoside in the particular step used, on a molar basis. As with temperature, the catalyst concentration must be controlled to minimize the formation of color bodies and polydextrose. It is preferred to use a catalyst that is easily neutralized with an alkaline substance to effect termination of the reaction of the present process. Otherwise, the resulting isolated product could include an unacceptable amount of color bodies. An aliphatic or aromatic sulfonic acid catalyst, for example, a toluene sulfonic acid catalyst, has been found suitable for the process described herein. Other commercially available catalysts like methane sulfonic acid, benzene sulfonic acid, alkyl benzene sulfonic acid, alkyl naphthalene sulfonic acid, sulfosuccinic acid, or lower alkyl substituted sulfonic acids like xylene or cumene sulfonic acids may also be suitable.

To neutralize the catalyst, an alkaline substance, preferably an alkali metal hydroxide, such as sodium hydroxide, or an alkali metal carbonate, such as sodium carbonate, is used in an amount about equal, on a stoichiometric basis, to the amount of material needed to neutralize the catalyst. If a toluene sulfonic acid catalyst is used, one mole of the alkaline substance may, for example, react with one mole of catalyst. If one mole of the alkaline substance reacts with one mole of the catalyst, for example when sodium hydroxide is used to neutralize the catalyst, then an amount of the alkaline material about equal to the amount of catalyst, on a molar basis, is used to neutralize the catalyst. Such a neutralization reaction would yield one mole of neutral sodium toluene sulfonate for each mole of catalyst and alkaline substance used.

It should be appreciated that when other acid catalysts are used—such as sulfuric acid—they may not be as easily neutralized. The inability to determine and control neutrality with such a catalyst could cause the production of an alkenyl glycoside product having an unacceptable color for certain uses. For example, sulfuric acid may form esters with the unsaturated alcohol, the alkenyl glycoside and the reducible monosaccharide or composition hydrolyzable to reducible a monosaccharide present. These acidic sulfate esters themselves may cause the production of color bodies. Just as important, because the amount of these esters may be variable and difficult to determine, it may be nearly impossible to calculate the amount of alkaline material needed to neutralize the sulfuric acid and its half acid esters present and to maintain neutrality during a subsequent isolation step. If too much alkaline material is used, such as when stoichiometric amounts of a basic compound are applied to a sulfuric acid catalyzed product, then the excess alkalinity could cause degradation of reducible monosaccharide or composition hydrolyzable to reducible a monosaccharide, forming base catalyzed and promoted reactions and volatile and non-volatile color bodies. Similarly, if insufficient alkaline material is added, then acid catalyzed side reactions may cause the production of color bodies during handling and/or undesired polymerization of the resulting product during isolation.

In order to reduce the amount of colored products, it is desirable to maintain a certain minimum level of water in the reaction mixture at all times. For example, when glucose monohydrate is the starting material, this water retention helps solubilize the glucose, prevents the degradation of the glucose, which could otherwise accelerate, and slows down color body forming condensation. In conjunction with maintaining the vacuum pressure within a specified range, it has been found that use of glucose monohydrate as the monosaccharide starting material helps ensure that a preferred amount of water will be present in the mixture at the time the reaction is started.

When glucose monohydrate is used, the monosaccharide as a slurry in the fatty alcohol is held at a pressure between about 20 mm Hg and about 100 mm Hg, preferably between about 30 mm Hg and about 60 mm Hg, prior to the introduction of the glycosidation catalyst. Glucose monohydrate cannot be heated or reacted directly with alcohols in the presence of the acid catalyst because of the large amount of water initially present in the mixture. The presence of this combination of water and acid could cause the production of unwanted by-products, in particular melted and/or agglomerated dextrose or polydextrose, and could retard the desired glycosidation reaction because of its reversibility. To remove the excess water, the mixture is heated, in the absence of acid, for between about 0.5 and about 2 hours, until most of the water of hydration is evaporated. The temperature applied to evaporate the water preferably is between about 60° C. and about 70° C. Although most of the water is removed by evaporation, thus ensuring that agglomerated dextrose formation will not occur, enough water is retained in the mixture, such as between 0.1% and 0.25% based upon the weight of the reaction mixture, to ensure that later glucose degradation and polymerization of dehydration products is minimized. The mixture is then heated to a temperature preferably between about 90° C. and about 120° C., over a period of between about 0.5 and about 1.5 hours. The catalyst is then added to start the reaction. After the reaction begins, the water produced is eventually balanced by the water removed by evaporation. When this steady state is reached, enough water remains in the reaction mixture to inhibit glucose degradation and polymerization of dehydration in products.

If anhydrous glucose is used instead of glucose monohydrate as the monosaccharide starting material, there will be little water in the mixture before the reaction begins. After the reaction begins, water will gradually build up in the reaction mixture until the water produced becomes balanced by the water evaporated. At this time, the reaction mixture includes enough water to inhibit glucose degradation. It should be appreciated that the actual amount of water present in the reaction mixture as the reaction takes place depends upon the pressure, type of alcohol used, the temperature applied and may also depend upon the glucose starting material. It should also be appreciated that when glucose monohydrate is used as the starting material, instead of anhydrous glucose, the amount of water required to prevent or minimize glucose degradation is present in the mixture prior to the beginning of the reaction; whereas when anhydrous glucose is the starting material, the amount of water needed to help solubilize glucose and prevent or minimize glucose degradation may not be generated until after the reaction has proceeded for a period of time.

When anhydrous glucose or glucose monohydrate is used as the starting material, it has been found that an acceptable product may also be produced without having to allow the reaction to proceed until substantially all of the glucose has reacted. As an alternative to allowing the reaction to progress to completion, one may choose to allow the reaction to proceed until, for example, about 0.1% to about 3% of the glucose starting material remains. The time needed to achieve this extent of reaction would be shorter than the time required to achieve complete consumption of glucose. The advantage from shortening the reaction time is that the less time the reaction proceeds, the more kinetically controlled the process and the lesser the amount of undesirable by-products produced. To ensure that the remaining glucose will not react to produce unwanted by-products, an amount of sodium borohydride may be added. Functionally, the sodium borohydride reduces the excess glucose to sorbitol, and other reducing sugars to their corresponding glycitols. Using sodium borohydride to reduce the excess glucose has been found in some cases to be more efficient than to bleach the product that would otherwise result if the glucose had not been converted to sorbitol.

In the second step of transglycosidation, a hydrocarbyl glycoside is employed as the starting material, for example, a butyl glucoside/glucose mixture may be used as the starting material. Such a mixture may be made in a first step by admixing butanol with glucose, preferably in a butanol-to-glucose molar ratio of about 2.5 to about 8.0. When glucose monohydrate is combined with butanol, vacuum is applied at a pressure between about 100 mm Hg and about 300 mm Hg, preferably between about 125 mm Hg and about 285 mm Hg. To remove a portion of the water of hydration initially present in the mixture, the mixture is heated for between about 0.5 and about 2.0 hours. The temperature applied to distill the water is preferably between about 60° C. and about 90° C. About 0.2% to about 2.0% water, based on the total weight of the mixture, remains in the mixture. Both water and butanol are removed by distillation under these conditions. The distilled butanol may be returned to the mixture after dehydration, preferably by distillation.

The pressure may then be increased to between about 450 mm Hg to about 750 mm Hg. The mixture is then heated over a period of between about 0.5 hours to about 1.5 hours to a temperature between about 100° C. and about 115° C. An acid catalyst that may be completely neutralized with stoichiometric amounts of an alkaline substance is added in an amount between about 0.5% and about 2.0%, based on the amount of glucose used, on a molar basis. The reaction will produce a butyl glucoside product and a water by-product. The reaction should be continued until the dextrose has dissolved. This should require approximately 1 to 5 hours. During this period, both water and butanol are removed by distillation. The distilled butanol may be returned to the reaction mixture after dehydration, preferably by distillation.

Alternatively, a butyl glucoside/glucose mixture may be made by admixing butanol with anhydrous glucose or glucose monohydrate, preferably in a butanol-to-glucose molar ratio of from about 2.5 to about 8.0, along with an acid catalyst that may be completely neutralized with stoichiometric amounts of an alkaline substance. Because of the water of hydration initially present in the mixture when glucose monohydrate is used, and because the reaction will produce a butyl glucoside product and a water by-product, the pressure must be reduced to a level sufficient to enable removal of a substantial amount of water. The pressure applied will allow about 0.2% to 2.0% water, based upon the total weight of the reaction mixture, to remain in the mixture, and preferably should be between about 450 mm Hg to about 750 mm Hg. The catalyst should be added in an amount between about 0.5% and about 2.0% based on the amount of glucose used, on a molar basis.

After the butanol, glucose and catalyst have been combined and the pressure reduced, the mixture is heated to a temperature between about 100° C. and about 115° C., to enable the butanol to react with the glucose. The reaction should be continued until the dextrose has dissolved. This should require approximately 1 to 6 hours. During this period, both water and butanol are removed by distillation. The distilled butanol may be returned to the reaction mixture after dehydration, preferably by distillation.

Once the glucose has dissolved, this butyl glucoside/glucose mixture, which makes up the starting material for the process described in this embodiment, should contain between about 24% and 50% butyl glucosides, between about 1% and about 5% glucose, and between about 45% and 75% butanol. To this mixture is then added an unsaturated monohydric alcohol containing 10 to 30 carbons. This C 10-30 unsaturated carbon monohydric alcohol replaces the butanol as it is being distilled from the reaction mixture. The ratio of unsaturated monohydric alcohol-to-glucose that was admixed with the butanol is about 2.5 to about 6 on a molar basis. During this step in the process the pressure is preferably reduced to between about 20 mm Hg and about 100 mm Hg at a relatively constant rate over a period of between about 1.5 to about 4 hours. This enables the removal of a substantial amount of the butanol from the reaction mixture. After the 10-30 carbon alcohol is added, the reaction preferably proceeds for an additional 0.5 to 6 hours. After this period of time, the residual butanol should have been reduced to between about 1% and about 2.5% of the reaction mixture, by weight, and the residual butyl glycosides (on a dry solids basis) should have been reduced to between about 2% and about 8% of the reaction mixture, by weight. At this point in the process, a sufficient amount of an alkaline substance, preferably sodium hydroxide, is added to neutralize the catalyst. The residual unreacted alcohol is then removed from the reaction mixture through evaporation or some equivalent means. The resulting product should contain between about 80% and about 95% alkylglycosides, about 2% and about 13% polydextrose, about 1% and about 3% nonpolar by-products, and about 2% and about 8% butyl glycosides.

The metathesis-derived hydrocarbyl unsaturated ester, preferably a $C_{10}$-$C_{30}$ unsaturated alkyl ester, more preferably a $C_{10}$-$C_{20}$ unsaturated alkyl ester, and even more preferably a $C_{10}$-$C_{17}$ unsaturated alkyl ester, used to make a metathesis-derived unsaturated fatty alcohol employed in the method described herein to produce an alkenyl glycoside product, is derived from metathesis of a natural oil. Preferably, the hydrocarbyl unsaturated ester is an unsaturated alkyl ester. Traditionally, these materials, particularly the short-chain alkyl esters (e.g., methyl 9-decenoate or methyl 9-dodecenoate), have been difficult to obtain except in lab-scale quantities at considerable expense. However, because of the recent improvements in metathesis catalysts, these esters are now available in bulk at reasonable cost. Thus, the hydrocarbyl unsaturated esters are conveniently generated by self-metathesis of natural oils or cross-metathesis of natural oils with olefins, preferably α-olefins, and particularly ethylene, propylene, 1-butene, 1-hexene, 1-octene, and the like.

Non-limiting examples of procedures for making hydrocarbyl unsaturated esters by metathesis are disclosed in WO 2008/048522, the contents of which are incorporated herein by reference. In particular, Examples 8 and 9 of WO 2008/048522 may be employed to produce methyl 9-decenoate and methyl 9-dodecenoate. Suitable procedures also appear in U.S. Pat. Appl. Publ. No. 2011/0113679, the teachings of which are incorporated herein by reference.

Preferably, at least a portion of the hydrocarbyl unsaturated ester has "Δ9" unsaturation, that is, the carbon-carbon double bond in the ester is at the 9-position with respect to the ester carbonyl. In other words, there are preferably seven carbons between the ester carbonyl group and the olefin group at C9 and C10. For the $C_{11}$ to $C_{17}$ esters, an alkyl chain of 1 to 7 carbons, respectively is attached to C10. Preferably, the unsaturation is at least 1 mole % trans-Δ9, preferably at least 25 mole % trans-Δ9, more preferably at least 50 mole % trans-Δ9, and even more preferably at least 80% trans-Δ9. The unsaturation may be greater than 90 mole %, greater than 95 mole %, or even 100% trans-Δ9. In contrast, naturally sourced fatty esters that have $\Delta^9$ unsaturation, e.g., methyl oleate, usually have ~100% cis-isomers.

Although a high proportion of trans-geometry (particularly trans-Δ9 geometry) may be desirable in the metathesis-derived unsaturated alcohol employed in the method described herein, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal., A* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-Δ9 geometry.

Suitable metathesis-derived hydrocarbyl unsaturated esters are derived from carboxylic acids. Examples include esters derived from 9-decenoic acid, 9-undecenoic acid, 9-dodecenoic acid 9-tridecenoic acid, 9-tetradecenoic acid, 9-pentadecenoic acid, 9-hexadecenoic acid, 9-heptadecenoic acid, and the like.

Usually, cross-metathesis or self-metathesis of the natural oil is followed by separation of an olefin stream from a modified oil stream, typically by stripping or distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is cross-metathesized with an α-olefin and the product mixture is transesterified, the resulting hydrocarbyl unsaturated ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. The unsaturated alkyl esters are readily separated from each other and easily purified by fractional distillation. These hydrocarbyl unsaturated esters, preferably alkyl esters are excellent starting materials for making the inventive unsaturated alcohol derivative compositions.

Natural oils suitable for use as a feedstock to generate the hydrocarbyl unsaturated esters from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, linseed oil, tung oil, jatropha oil, mustard oil, pennycress oil, camellina oil, coriander oil, almond oil, wheat germ oil, bone oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, canola oil, and rapeseed oil.

A modified natural oil, such as a partially hydrogenated vegetable oil or an oil modified by a fermentation process, can be used instead of or in combination with the natural oil. When natural oil is partially hydrogenated or modified by fermentation, the site of unsaturation can migrate to a variety of positions on the hydrocarbon backbone of the fatty ester moiety. Because of this tendency, when the modified natural oil is self-metathesized or is cross-metathesized with an olefin, the reaction products will have a different and generally broader distribution compared with the product mixture generated from an unmodified natural oil. However, the products generated from the modified natural oil are similarly converted to inventive unsaturated alcohol derivative compositions. In certain embodiments, the naturally occurring oil may be refined, bleached, and/or deodorized.

The other reactant in the cross-metathesis reaction is an olefin. Suitable olefins are internal or α-olefins having one or more carbon-carbon double bonds, and having between about 2 to about 30 carbon atoms. Mixtures of olefins can be used.

Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used for self-metathesized reactions. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

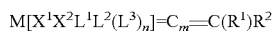

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

Heterogeneous catalysts suitable for use in the self- or cross-metathesis reaction include certain rhenium and molybdenum compounds as described, e.g., by J. C. Mol in Green Chem. 4 (2002) 5 at pp. 11-12. Particular examples are catalyst systems that include $Re_2O_7$ on alumina promoted by an alkylating cocatalyst such as a tetraalkyl tin, lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein. See also *J. Org. Chem.* 46 (1981) 1821; *J. Catal.* 30 (1973) 118; *Appl. Catal.* 70 (1991) 295; *Organometallics* 13 (1994) 635; *Olefin Metathesis and Metathesis Polymerization* by Ivin and Mol (1997), and *Chem. & Eng. News* 80(51), Dec. 23, 2002, p. 29, which also disclose useful metathesis catalysts. Illustrative examples of suitable catalysts include ruthenium and osmium carbene catalysts as disclosed in U.S. Pat. Nos. 5,312,940, 5,342,909, 5,710,298, 5,728,785, 5,728,917, 5,750,815, 5,831,108, 5,922,863, 6,306,988, 6,414,097, 6,696,597, 6,794,534, 7,102,047, 7,378,528, and U.S. Pat. Appl. Publ. No. 2009/0264672 A1, and PCT/US2008/009635, pp. 18-47, all of which are incorporated herein by reference. A number of metathesis catalysts that may be advantageously employed in metathesis reactions are manufactured and sold by Materia, Inc. (Pasadena, Calif.).

The metathesis-derived unsaturated fatty alcohols employed in the method described herein are made by reacting a metathesis-derived hydrocarbyl unsaturated fatty ester, preferably a $C_{10}$-$C_{30}$ unsaturated alkyl ester, more preferably a $C_{10}$-$C_{20}$ unsaturated alkyl ester, and even more preferably a $C_{10}$-$C_{17}$ unsaturated alkyl ester, with a reducing agent. As used herein, "metathesis-derived unsaturated fatty alcohols" typically have a hydrocarbyl chain length of between 10 and 30 carbon atoms. In some embodiments, the unsaturated alcohols have the general structure of R—CH=CH—$(CH_2)_7$—$CH_2OH$, wherein R is H, $(CH_2)_{1-7}CH_3$ or $(CH_2)_{1-7}CH_2OH$. In some preferred embodiments, the metathesis-derived unsaturated alcohol is 9-decen-1-ol, 9-dodecen-1-ol, 9-tridecen-1-ol, 9-pentadecen-1-ol, and 9-octadecen-1-ol or 9-octadecen-1,18-diol more preferably the metathesis-derived unsaturated alcohol is 9-decen-1-ol, 9-dodecen-1-ol, 9-octadecen-1-ol or 9-octadecen-1,18-diol.

Reduction of metathesis-derived hydrocarbyl unsaturated esters, preferably unsaturated alkyl esters, to produce the metathesis-derived unsaturated fatty alcohols employed in the method described herein is performed using well-known catalysts or reagents and procedures. The reducing agent is typically either a hydride reducing agent (sodium borohydride, lithium aluminum hydride, or the like) or molecular hydrogen in combination with a metal catalyst, frequently copper and/or zinc in combination with chromium, or a silane compound in combination with a metallic complex catalyst (see, e.g., U.S. Pat. Nos. 2,865,968; 3,193,586; 4,804,790; 5,124,491; 5,672,781; 5,831,133, 6,683,224; 7,169,959 and 7,208,643, and Mimoun, H. J., *J. Org. Chem.* 1999, 64, 2582-2589 the teachings of which are incorporated herein by reference).

The skilled person will appreciate that the reduction process, particularly when transition metal catalysts are used to convert the hydrocarbyl unsaturated fatty esters to fatty alcohols, can induce some degree of isomerization or migration of the carbon-carbon double bond from its original position. Moreover, because ester hydrogenation catalysts are not always completely selective, a minor proportion of the carbon-carbon double bonds, typically 10% or less, might be hydrogenated during the ester reduction, resulting in a mixed product that may have up to 10% of saturated fatty alcohols in addition to the desired unsaturated fatty alcohols.

In some embodiments, the metathesis process to prepare the unsaturated fatty alcohols employed in the method described herein is characterized in that a carbonyl compound, in particular, a hydrocarbyl unsaturated fatty ester, is reacted with stoichiometric amounts of a silane compound, in the presence of a catalyst system prepared from a metallic complex and a reducing agent. Preferably, the unsaturated fatty alcohols comprise 9-decen-1-ol, 9-dodecen-1-ol, 9-octadecen-1-ol, or 9-octadecen-1,18-diol and the hydrocarbyl unsaturated ester comprises methyl-9-decenoate, methyl-9-dodecenoate or methyl-9-octadecen-1,18-dioate. The silane compound can be selected from the group consisting of alkyltrihydrosilanes, aryltrihydrosilanes, dialkyldihydrosilanes, diaryldihydrosilanes, trialkylhydrosilanes, triarylhydrosilanes, alkylhydrosiloxanes, arylhydrosiloxanes, polyalkylhydrosiloxanes and the like, individually or in combinations thereof. Preferably, the silane compound is polymethylhydrosiloxane. The catalyst system can be obtained in situ, in the reaction medium or be prepared separately, and comprises a metallic complex of general formula $MX_n$, wherein M represents a transition metal selected from the group consisting of zinc, cadmium, manganese, cobalt, iron, copper, nickel, ruthenium and palladium, X an anion comprising a halide, a carboxylate or any anionic ligand, wherein X is selected from the group consisting of chloride, bromide, iodide, carbonate, isocyanate, cyanide, phosphate, acetate, propionate, 2-ethylhexanoate, stearate or naphthenate of one of the above-mentioned metals, individually or in combinations thereof, and n is a number comprised between 1 and 4. In some embodiments, X will be reacted with a reducing agent selected from the group consisting of a hydride, wherein the hydride can be an alkaline hydride such as lithium, sodium or potassium hydride, or an alkaline earth hydride such as magnesium or calcium hydride, or a boron hydride such as $BH_3$, a metallic borohydride $MBH_4$ (where M is Li, Na, or K) or $M(BH_4)_2$ (where M is Mg, Zn, or Ca), an alkylborane $R_nBH(4-n)M$ (where R is alkyl, n is 1 to 3, M is alkaline metal), $a(RO)_n BH(4-n)M$ (where R is alkyl, n=1 to 3, where M is alkaline metal), or an aluminum hydride $AlH_3$, $AlH_nR_3$-n (where R is alkyl), $MAlH_4$ (M is Li, Na, K), $MAlH_n(OR)_4$-n (where M is Li, Na, or K), or an organic magnesium compound of formula RMgX (where R is alkyl, X is Cl, Br, or I), or an organic lithium compound RLi (where R is alkyl, for example $C_1$ to $C_4$ or aryl), individually or in combinations thereof, in order to generate the active catalyst. Preferably, M is zinc, X is a carboxylate such as 2-ethylhexanoate, n is 2, and the reducing agent is sodium borohydride, thus providing for a zinc 2-ethylhexanoate complex.

In some embodiments, the metallic complex and reducing agent, either individually, or in combination thereof, may be mixed with an inert organic solvent, for example, an ether such as methyl tertbutyl ether, diisopropyl ether, dioxane, tetrahydrofuran, ethylene glycol dimethyl ether, or an aliphatic hydrocarbon such as heptane, petroleum ether, octane, cyclohexane, or aromatic as benzene, toluene, xylene or mesitylene, individually or in combinations thereof. Preferably, the solvent is diisopropyl ether.

When the catalyst system is prepared in situ, the chosen metallic complex, (preferably zinc 2-ethylhexanoate) will be reacted with the reducing agent (preferably sodium borohydride) in an appropriate organic solvent (preferably diisopropyl ether) with the carbonyl compound (preferably an unsaturated hydrocarbyl ester such as methyl-9-decenoate or methyl-9-dodecenoate) at room temperature. After full release of the formed hydrogen, the carbonyl compound to be reduced will be introduced and heated, and thereafter the silane compound (preferably polymethylhydrosiloxane or PMHS) is added into the solution. The typical consumption of PMHS will be about 2.2 equivalents for the reduction of esters. The resulting solution is hydrolyzed by reacting the solution with an aqueous or alcoholic solution of a metallic base, such as sodium hydroxide, potassium hydroxide, calcium oxide or sodium carbonate (preferably potassium hydroxide), individually or in combinations thereof, and then adding an appropriate organic solvent. Once the hydrolysis is complete, formation of two phases is generally observed, with the desired alcohol being in the organic phase. This organic phase is then separated, washed, dried, and/or purified, as individual steps or in combination thereof, to produce the unsaturated alcohol.

In some embodiments, the unsaturated alcohol can be produced by the selective hydrogenation of the corresponding unsaturated fatty acid methyl ester. This hydrogenation can be carried out over bimetallic catalysts containing cobalt and tin, or ruthenium and tin. Other methods to produce unsaturated alcohols are provided in U.S. Pat. Nos. 5,364,986 and 6,229,056, the teachings of which are incorporated herein by reference.

Suitable hydrocarbyl unsaturated fatty esters can be generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of hydrocarbyl unsaturated fatty esters, preferably unsaturated fatty alkyl esters. The hydrocarbyl unsaturated fatty ester mixture can be purified to isolate particular fatty alkyl esters prior to making the unsaturated alcohols.

Some metathesis-derived unsaturated fatty alcohol compositions employed in the method described herein have the general structure:

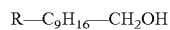

wherein R is H, $(CH_2)_{1-9}CH_3$, or $(CH_2)_{1-9}CH_2OH$.

Preferably, the fatty alcohol compositions have the general structure:

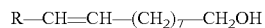

wherein R is H or $(CH_2)_{1-7}CH_3$ or $(CH_2)_{1-7}CH_2OH$

As noted above, it is understood that the glycosides produced in the method described above may be accompanied by the formation of polyglycosides in addition to the monoglycoside. Consequently, as employed herein, except where expressly stated otherwise, the term "glycoside" includes both the glycoside specified and also polyglycosides formed with it. When it is desired to prevent or minimize the formation of polyglycosides and any other undesirable side or competing reactions, the hydroxy groups can be protected by reacting them with protecting groups to prevent the hydroxy groups from entering into any side or competing reactions to produced unwanted products. Upon completion of the selective mono-glycosidation, the protecting groups are removed.

EXAMPLES

Example 1

Cross-Metathesis of Soybean Oil with 1-Butene

The following is exemplary of a method of cross-metathesis of soybean oil with 1-butene and the products obtained thereby. A clean, dry, stainless steel jacketed 5-gal. Parr reactor vessel equipped with a dip tube, overhead stirrer, internal cooling/heated coils, temperature probe, sampling valve, and headspace gas release valve is purged with argon to 15 psig. Soybean oil (SBO, 2.5 kg, 2.9 mol, Costco, MWn=864.4 g/mol, 85 weight % unsaturation as determined by gas chromatographic analysis ("by gc"), 1 hour argon sparged in 5-gal container) is added into the Parr reactor. The Parr reactor is then sealed and the SBO is purged with argon for 2 hours while cooling to 10° C. After 2 hours, the reactor is vented until the internal pressure reaches 10 psig. The dip tube valve on the reactor is connected to a 1-butene cylinder (Airgas, CP grade, 33 psig headspace pressure, >99 weight %) and re-pressurized to 15 psig of 1-butene. The reactor is vented again to 10 psig to remove residual argon in the headspace. The SBO is stirred at 350 rpm and 9-15° C. under 18-28 psig 1-butene until 3 mol 1-butene per SBO olefin bond is transferred into the reactor (approximately 2.2 kg 1-butene over approximately 4-5 hours). A toluene solution of [1,3-Bis-(2,4,6-trimethylphenyl)-2-imidazolidinylidene]dichlororuthenium(3-methyl-2-butenylidene)(tricyclohexylphosphine) (C827, Materia) is prepared in Fischer-Porter pressure vessel by dissolving 130 mg catalyst in 30 grams of toluene as a catalyst carrier (10 mol ppm per olefin bond of SBO) and is added to the reactor via the reactor dip tube by pressurizing the headspace inside the Fischer-Porter vessel to 50-60 psig with argon. The Fischer-Porter vessel and dip tube are rinsed with an additional 30 g toluene. The reaction mixture is stirred for 2.0 hours at 60° C. The reaction mixture is allowed to cool to ambient temperature while the gases in the headspace are vented. After the pressure is released, the reaction mixture is transferred to a 3-neck round bottom flask containing 58 g bleaching clay (2% w/w SBO, Pure Flow B80 CG) and a magnetic stir bar. The reaction mixture is treated by stirring at 85° C. under argon. After 2 hours, during which time any remaining 1-butene is allowed to vent, the reaction mixture is allowed to cool to 40° C. and filtered through a fritted glass filter. An aliquot of the product mixture is found by gas chromatographic analysis (following transesterification with 1% w/w NaOMe in methanol at 60° C.) to contain approximately 22 weight % methyl 9-decenoate, approximately 16 weight % methyl 9-dodecenoate, approximately 3 weight % dimethyl 9-octadecenedioate, and approximately 3 weight % methyl 9-octadecenoate (by GC).

Example 2

Production of methyl 9-octadecene-1,18-dioate by Metathesis

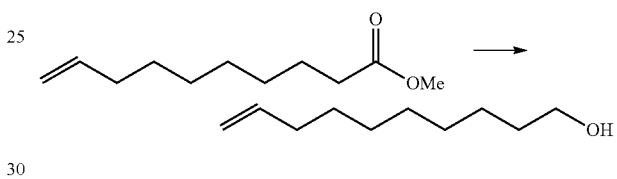

A dibasic ester composition is produced in accordance with the exemplary procedure below, including a crossmetathesis reaction between methyl 9-decenoate (9-decenoic acid methyl ester, 9-DAME) and methyl 9-dodecenoate (9-dodecenoic acid methyl ester, 9-DDAME). A 1.0:1.0 mole ratio mixture of 9-DAME and 9-DDAME (332 g) is charged to a 1 L round bottom flask and heated to 60° C. Pressure is adjusted to 100 mg Hg with ChemGlass diaphragm vacuum pump model CG-4812-30/and J-Kem Scientific Digital Vacuum Regulator Model 200 and stirring is initiated with a magnetic stir bar. After the system stabilizes at desired conditions, 80 ppm of C-827 (as toluene solution) is added (t=0 min). At approximately 15-20 min, the reaction starts bubbling vigorously and the pressure rises to approximately 500 mm Hg. Pressure restabilizes at 100 mm Hg after approximately 5-10 more minutes. At 180 min, an additional 40 ppm of the catalyst C-827 (as toluene solution) is added. Subsequently, the catalyst is deactivated with 25 equivalents tris hydroxymethyl phosphine (THMP) to C-827 at 80° C. for 120 min, THMP.

The catalyst is then removed by water extraction (5:1 oil to water). The composition is dried with MgSO4. Then, light FAME stripping is conducted at 1 mm Hg and approximately 100° C. The products from this reaction include a large fraction of 18:1 dibasic ester.

Example 3

Production of 9-decen-1-ol from the methyl-9-decenoate of Example 1

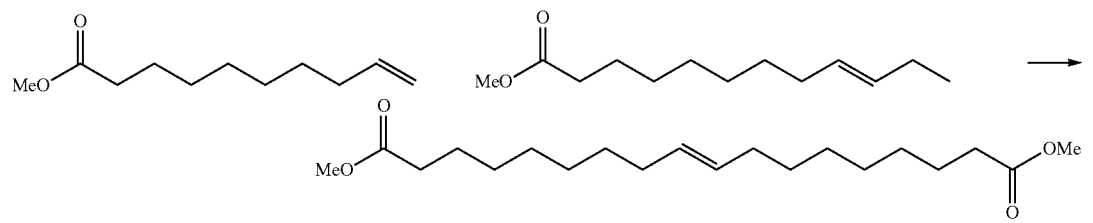

Methyl 9-decenoate (300 g, 1.63 mol) and tetrahydrofuran (500 mL) were added to a 2 L 3-necked round-bottom flask at 23° C. under an atmosphere of air. The flask was then fitted with a thermocouple temperature regulator with heating mantle, magnetic stirbar, and a stopper with nitrogen needle inlet. Through the headspace of the apparatus was passed $N_2$ (flow rate=2.5 ft$^3$/hr) for 10 minutes, and subsequently, the reaction was cooled with external cooling bath (ice/brine). Against positive nitrogen pressure, lithium aluminum hydride (30 g, 0.8 mol) was added, portionwise, while maintaining the internal temperature below 50° C. The total addition time was 45 minutes. The reaction was allowed to stir for another 2 hours (spot-to-spot by thin layer chromatography on SiO$_2$). The reaction mixture was carefully poured onto ice-chilled 1% aqueous HCl solution (~1 L) which was subsequently transferred to a separatory funnel. The product was extracted with ethyl acetate (400 mL). The organic layer was washed saturated NaCl solution (1×). The organic phase was dried with anhydrous magnesium sulfate, filtered, and concentrated by rotary evaporator (5 Torr, 60° C.) to provide the desired alcohol product as a colorless oil (245 g, 96% yield).

Example 4

Production of 9-dodecen-1-ol from the methyl 9-dodecenoate of Example 1

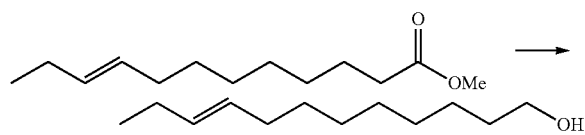

To a dry 2 L 3-neck round bottom flask fitted with a nitrogen inlet and outlet, thermocouple, condenser, mechanical stirrer and pressure-equalizing dropping funnel was added lithium aluminum hydride (30.10 g, 0.754 mol, 95% technical grade solid) in one portion, under a positive pressure of nitrogen. The metal hydride was suspended in anhydrous tetrahydrofuran (500 mL) and the mixture cooled on an ice bath. Methyl 9-dodecenoate (200 g, 0.942 mol) was added dropwise via addition funnel to the stirred lithium aluminum hydride suspension over 1 h at such a rate as to maintain the internal temperature below 50° C. When the reaction exotherm subsided, the external cooling bath was removed and the resulting viscous mixture was stirred for a further 8 h at ambient temperature. Complete consumption of starting material was confirmed by thin layer chromatography and by FTIR. The reaction was quenched by the careful addition of the reactor contents to a 4 L Erlenmeyer flask containing chilled concentrated aqueous sodium chloride (300 mL). The reactor was rinsed with ethyl acetate (100 mL) then 10% (v/v) aqueous sulfuric acid (100 mL); both rinse aliquots were combined with the reaction neutralization mixture. An additional aliquot of 10% (v/v) aqueous sulfuric acid was added to neutralize the aqueous phase then the biphasic neutralization mixture was transferred to a separatory funnel. The aqueous phase was partitioned and washed with ethyl acetate (100 mL×2). The combined organic phases were successively washed with concentrated aqueous sodium bicarbonate (100 mL), brine (100 mL), dried (MgSO$_4$) then filtered. The organic phase was concentrated in vacuo, giving 9-dodecen-1-ol (165 g, 95%) as clear, colorless oil.

Example 5

Production of 9-octadecene-1,18-diol from methyl 9-octadecene-1,18-dioate of Example 2

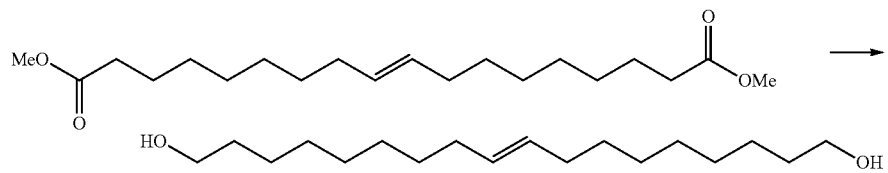

To a dry 1 L 3-neck round bottom flask fitted with a nitrogen inlet and outlet, thermocouple, condenser, mechanical stirrer and pressure-equalizing dropping funnel was added lithium aluminum hydride (4.20 g, 0.105 mol) in one portion, under a positive pressure of nitrogen. The metal hydride was suspended in anhydrous tetrahydrofuran (200 mL) and the mixture cooled to 10° C. on chilled water bath. 9-octadecen-1,18-dioc acid methyl ester (20.00 g, 0.0587 mol, as a solution in 100 mL anhydrous tetrahydrofuran) was added dropwise via addition funnel to the stirred LAH suspension over 1 h. An exothermic reaction was observed. When the reaction exotherm subsided, the external cooling bath was removed and the resulting viscous mixture was stirred for 16 h at ambient temperature. Complete consumption of starting material was confirmed by thin layer chromatography and FTIR. The reaction was then quenched by the careful addition of the reactor contents to a 1 L Erlenmeyer flask containing chilled concentrated aqueous sodium chloride (200 mL), under a flow of nitrogen. The reactor was rinsed with ethyl acetate (50 mL) then 10% (v/v) aqueous sulfuric acid (50 mL); both rinse aliquots were combined with the reaction neutralization mixture. An aliquot additional of 10% (v/v) aqueous sulfuric acid was added to neutralize the aqueous phase. The biphasic neutralization mixture was transferred to a separatory funnel. The aqueous phase was separated and washed with ethyl acetate (50 mL×2). The combined organic phases were successively washed with concentrated aqueous sodium bicarbonate (50 mL), brine (50 mL), dried (MgSO$_4$) then filtered. The organic phase was concentrated in vacuo, giving 9-octadecen-1,18-diol (15.30 g, 91.5%) as a white solid. Further purification was not required.

Example 6

Direct Glycosidation of 9-dodecen-1-ol with Glucose

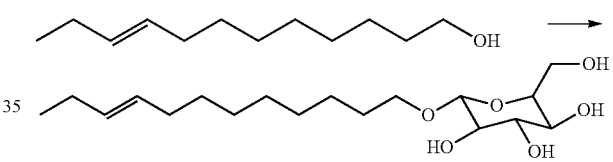
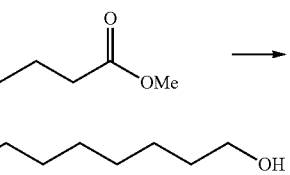

Dextrose (25.0 g, 0.139 mol, anhydrous) and 9-dodecenol (153.4 g, 0.832 mol) were charged to a dry 250 mL three-neck round bottom flask fitted with a Dean-Stark trap and condenser. The resulting suspension was warmed to an internal temperature of 110° C. under an inert atmosphere of N$_2$ with vigorous magnetic stirring. A catalytic amount of p-toluenesulfonic acid monohydrate (0.132 g, 0.695 mmol, as a solution in 0.20 mL nBuOH and 0.10 mL deionized water) was added in one portion via syringe. A partial vacuum (650 torr; slight sweep of N$_2$) was then applied to the top of the Dean-Stark condenser. The reaction slurry was digested at 110° C. for the duration of the reaction. Over 6.5 h, the pressure in the reactor was incrementally decreased from 650 to a 20 torr, a final pressure at which the reaction was digested for an additional 0.5 h. After 7 h, 2.61 mL water (0.145 mol) was collected in the Dean-Stark trap, indicating complete consumption of dextrose. The amber, opaque reaction mixture was neutralized by the addition of 50% aqueous sodium hydroxide (0.278 g, 0.695 mmol, equimolar versus the pTSA catalyst charged). The reactor was cooled to ambient temperature, restored to ambient pressure (N$_2$) then fitted with a short-path distillation apparatus. Excess 9-dodecenol was removed via vacuum distillation (137-180° C., 6 torr), the bulk of the residual C$_{1-2}$ alcohol being retrieved at a distillation pot temperature of 137-143° C. 9-dodecenyl polyglucoside was obtained as a glassy, amber solid, on cooling to ambient temperature. GC-MS analysis of the product revealed an oligomer distribution consisting of 65.5% alkenyl monoglucoside, 24.6% diglucoside, 7.0% triglucoside and 2.9% tetraglucoside. GC sample preparation: Approximately 20 mg of 9-dodecenyl polyglucoside was digested at ambient temperature in 0.30 mL N,O-bis(trimethylsilyl)trifluoroacetamide and 0.70 mL N,N-dimethylformamide for at least 1 h prior to submission to chromatographic analysis.

Example 7

Direct Glycosidation of 1-butanol with Glucose

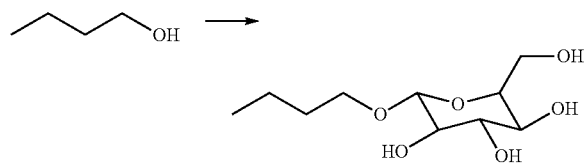

Dextrose (35.0 g, 0.194 mol, anhydrous) and 1-butanol (86.4 g, 1.16 mol) were charged to a dry 250 mL three-neck round bottom flask fitted with a Dean-Stark trap and condenser. The resulting suspension was warmed to an internal temperature of 110° C. under an inert atmosphere of N$_2$ with vigorous magnetic stirring. A catalytic amount of p-toluenesulfonic acid monohydrate (0.185 g, 0.971 mmol, as a solution in 0.20 mL nBuOH and 0.10 mL deionized water) was added in one portion via syringe. A partial vacuum (650 torr; slight sweep of N$_2$) was then applied to the top of the Dean-Stark condenser. Wet butanol (26.99 g) was collected in the Dean-Stark trap over the course of 60 minutes. During this time, the starting colorless suspension became a colorless, clear homogenous mixture containing butyl polyglucosides in excess butanol. This material was used in the subsequent transglycosidation with 9-dodecen-1-ol, as described in the following example.

Example 8

Transglycosidation of the glucoside produced in Example 7

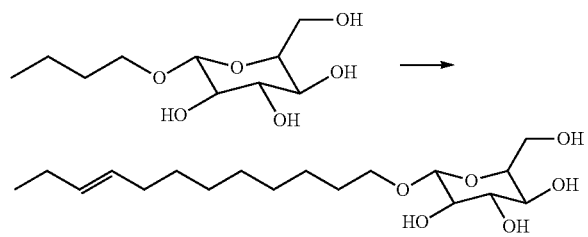

To the above butanolic solution of intermediate butyl polyglucoside was added 9-dodecen-1-ol (89.6 g, 0.486 mol) in approximately 30 g portions via syringe at ca. 45 min intervals to the intermediate butyl polyglucoside at 110° C. Over this 2.5 h addition/reaction period, the reactor pressure was decreased from 650 to 20 torr. Upon complete addition of 9-dodecenol, the reaction was digested for a further 30 min at 110° C. and 20 torr, until the removal of nBuOH into the Dean-Stark trap ceased. 50% aqueous potassium hydroxide (0.0544 g, 0.971 mmol, equimolar versus the pTSA catalyst charged) was added via syringe to quench the reaction. A clear, light orange viscous fluid was obtained. The reactor was cooled to ambient temperature, restored to ambient pressure (N2) then fitted with a short-path distillation apparatus. A sample of the crude material was submitted for analysis by reverse-phase HPLC, GC-MS. Excess 9-dodecen-1-ol was removed via vacuum distillation (137-180° C., 6 torr), the bulk of the residual C$_{1-2}$ alcohol being retrieved at a distillation pot temperature of 137-145° C. 9-dodecenyl polyglucoside was obtained as a tacky, light orange solid. GC-MS analysis of the product revealed an oligomer distribution consisting of 62.2% alkyl monoglucosides (22.2% butyl monoglucoside and 40.0% 9-dodecenyl monoglucoside) and 0.2% residual glucose. GC sample preparation: Approximately 20 mg of 9-dodecenyl polyglucoside was digested at ambient temperature in 0.30 mL N,O-bis(trimethylsilyl)trifluoroacetamide and 0.70 mL N,N-dimethylformamide for at least 1 h prior to submission to chromatographic analysis.

While the invention has been explained in relation to various embodiments and examples, it is to be understood that various modifications thereof will become apparent to those skilled in the art upon reading the specification. Therefore, it is to be understood that the invention disclosed herein includes any such modifications that may fall within the scope of the appended claims.

We claim:

1. A method for preparing an alkenyl glycoside, comprising reacting an unsaturated fatty alcohol with a reducible monosaccharide or a composition hydrolyzable to a reducible monosaccharide, wherein the reacting is performed in the presence of an acid catalyst and under conditions sufficient to form the alkenyl glycoside or hydrocarbyl glycoside, and wherein the unsaturated fatty alcohol is 9-decen-1-ol, 9-dodecen-1-ol, 9-tridecen-1-ol, 9-pentadecen-1-ol, or 9-octadecen-1,18-diol.

2. The method of claim 1 wherein the reducible monosaccharide is at least one of glucose, mannose, galactose, talose, allose, ribose, or any and the monohydrate forms of any thereof.

3. The method of claim 1 wherein the reducible monosaccharide is glucose.

4. The method of claim 1 wherein the composition hydrolyzable to a reducible monosaccharide comprises at least one of starch, maltose, sucrose, lactose, melibose, raffinose methyl glucosides, butyl glucosides, or anhydro sugars.

5. The method of claim 1 wherein the mole ratio of the metathesis-derived unsaturated fatty alcohol to reducible monosaccharide or composition hydrolyzable to a reducible monosaccharide is in the range of from 3:1 to 10:1.

6. The method of claim 1 wherein the mole ratio of the metathesis-derived unsaturated fatty alcohol to reducible monosaccharide or composition hydrolyzable to a reducible monosaccharide is in the range of from 5:1 to 7:1.

7. The method of claim 1, wherein the unsaturated fatty alcohol is 9-decen-1-ol.

8. The method of claim 1, wherein the unsaturated fatty alcohol is 9-dodecen-1-ol.

9. The method of claim 1, wherein the unsaturated fatty alcohol is 9-tridecen-1-ol.

10. The method of claim 1, wherein the unsaturated fatty alcohol is 9-pentadecen-1-ol.

11. The method of claim 1, wherein the unsaturated fatty alcohol is 9-octadecen-1,18-diol.

* * * * *